(12) United States Patent
Spehr et al.

(10) Patent No.: US 12,151,098 B2
(45) Date of Patent: Nov. 26, 2024

(54) ANCHOR SYSTEM FOR RETAINING A DEVICE IN TISSUE

(71) Applicant: INCUBE LABS, LLC, San Jose, CA (US)

(72) Inventors: Paul Spehr, San Antonio, TX (US); Katherine Pitts, San Antonio, TX (US); Isabell Pina, San Antonio, TX (US); Charles Gregory Nelson, New Braunfels, TX (US); Kenneth R. Cosgrove, San Antonio, TX (US)

(73) Assignee: InCube Labs, LLC, San Jose, CA (US)

( * ) Notice: Subject to any disclaimer, the term of this patent is extended or adjusted under 35 U.S.C. 154(b) by 407 days.

(21) Appl. No.: 17/610,094

(22) PCT Filed: May 7, 2020

(86) PCT No.: PCT/US2020/031907
§ 371 (c)(1),
(2) Date: Nov. 9, 2021

(87) PCT Pub. No.: WO2020/227551
PCT Pub. Date: Nov. 12, 2020

(65) Prior Publication Data
US 2022/0241586 A1 Aug. 4, 2022

Related U.S. Application Data

(60) Provisional application No. 62/845,808, filed on May 9, 2019, provisional application No. 62/845,816, filed on May 9, 2019, provisional application No. 62/845,819, filed on May 9, 2019.

(51) Int. Cl.
*A61N 1/05* (2006.01)
*A61M 25/04* (2006.01)
*A61N 1/36* (2006.01)

(52) U.S. Cl.
CPC ........... *A61N 1/0558* (2013.01); *A61M 25/04* (2013.01); *A61N 1/36071* (2013.01)

(58) Field of Classification Search
CPC .................................... A61N 1/0558
See application file for complete search history.

(56) References Cited

U.S. PATENT DOCUMENTS

| | | |
|---|---|---|
| 2003/0199962 A1 | 10/2003 | Struble et al. |
| 2008/0103570 A1 | 5/2008 | Gerber |
| 2008/0103573 A1* | 5/2008 | Gerber ................ A61N 1/0536 607/116 |
| 2008/0183257 A1 | 7/2008 | Imran et al. |
| 2010/0256696 A1* | 10/2010 | Schleicher ........... A61N 1/0558 607/116 |
| 2011/0313427 A1* | 12/2011 | Gindele ............. A61N 1/36007 607/116 |

(Continued)

OTHER PUBLICATIONS

International Search Report for Application No. PCT/US2020/031907, dated Jul. 15, 2020, 3 pages.

(Continued)

*Primary Examiner* — Paula J Stice
(74) *Attorney, Agent, or Firm* — Brooks Kushman P.C.

(57) ABSTRACT

A lead device is provided for a medical treatment apparatus, where the lead device includes mechanisms for anchoring the lead device in tissue.

18 Claims, 10 Drawing Sheets

(56) References Cited

U.S. PATENT DOCUMENTS

| | | | |
|---|---|---|---|
| 2014/0296954 A1 | 10/2014 | Wells | |
| 2015/0297882 A1* | 10/2015 | Barker | A61N 1/0558 |
| | | | 607/116 |
| 2016/0082247 A1* | 3/2016 | Black | A61N 1/0539 |
| | | | 607/116 |
| 2017/0043155 A1 | 2/2017 | Marshall et al. | |

OTHER PUBLICATIONS

Written Opinion of the International Search Authority for Application No. PCT/US2020/031907, dated Jul. 15, 2020, 5 pages.

* cited by examiner

```
┌─────────────────────────────────────────────────────────────────────┐
│ On A Tubular Length, Forming, While The Tubular Length Is In A First │
│ Radial Orientation, A First Pair Of Voids, Each Void Of The First    │
│ Pair Being Diametrically Aligned                                     │
│                                                              510     │
└─────────────────────────────────────────────────────────────────────┘
                                  │
                                  ▼
┌─────────────────────────────────────────────────────────────────────┐
│ On The Tubular Length, Forming, While The Tubular Length Is In A     │
│ Second Radial Orientation, A Second Pair Of Voids, Each Void Of The  │
│ Second Pair Being Diametrically Aligned                              │
│                                                              520     │
└─────────────────────────────────────────────────────────────────────┘
                                  │
                                  ▼
┌─────────────────────────────────────────────────────────────────────┐
│ Separate One Or More Notched Anchors From The Tubular Length         │
│                                                              530     │
└─────────────────────────────────────────────────────────────────────┘
                                  │
                                  ▼
┌─────────────────────────────────────────────────────────────────────┐
│ Affix Notched Anchors To Lead Shaft                                  │
│                                                              540     │
└─────────────────────────────────────────────────────────────────────┘
```

FIG. 5

ANCHOR SYSTEM FOR RETAINING A DEVICE IN TISSUE

CROSS-REFERENCE TO RELATED APPLICATIONS

This application is the U.S. National Phase of PCT Application No. PCT/US2020/031907 filed on May 7, 2020, which claims the benefit of U.S. Provisional Application No. 62/845,808, filed on May 9, 2019, U.S. Provisional Application No. 62/845,816, filed on May 9, 2019, and U.S. Provisional Application No. 62/845,819, filed on May 9, 2019, the disclosures of which are hereby incorporated in their entirety by reference herein.

FIELD

Embodiments relate to anchoring mechanisms for an implanted medical device. Embodiments include permanent anchoring mechanisms, or a combination of permanent and dissolvable anchoring mechanisms, to anchor the device in tissue.

BACKGROUND

With advances in medical technology there has been an increasing use of various implantable biomedical devices, such as, for example, for delivering stimulatory and other electrical signals to tissue for the treatment of various medical conditions. Many of these devices employ a cord, catheter, lead or other device extended into tissue within an animalia body, for purposes of applying medical treatment through a treatment region of the device. For example, in some medical applications, an electrode is provided at the distal end of a device, and the device is introduced into the body with the distal end being advanced to reach a target region. In such applications, the target region may be adjacent to a nerve for electrical stimulation to the nerve, and relatively precise positioning of the electrode near the nerve may be important for the treatment to be effective.

Additionally, in many medical applications, a device for such medical applications may be maintained in the body for an extended period of time. For example, a device for providing stimulation for a medical treatment can be maintained in the body for days, weeks or even indefinitely, depending on the treatment provided. In such applications, the length of time that the device remains in place to stimulate the target region can extend past a period after which the body begins to react to the introduction and continued presence of the device. The physiological reactions can include, for example, movement or settlement of tissue surrounding the device, as well as fluid build-up and/or formation of scar tissue in an area around the device. Such physiological reactions can cause movement (e.g., migration) of the device, which can result in an effectiveness of the medical treatment being reduced, delivery of stimulation to the wrong tissue, an allergic reaction, or other unwanted immune response and/or infection of the implantation site. Further, body movement can also result in movement of the device. Thus, there is a need for anchoring of implanted devices within the body at the target region to resist movement of the implanted devices.

SUMMARY

Various embodiments include a medical treatment apparatus including protruding anchoring mechanisms to anchor a portion of the apparatus in tissue.

BRIEF DESCRIPTION OF THE DRAWINGS

FIG. 5 illustrates an example of an embodiment of a method for forming and applying notched anchors.

DETAILED DESCRIPTION

Figure 1:
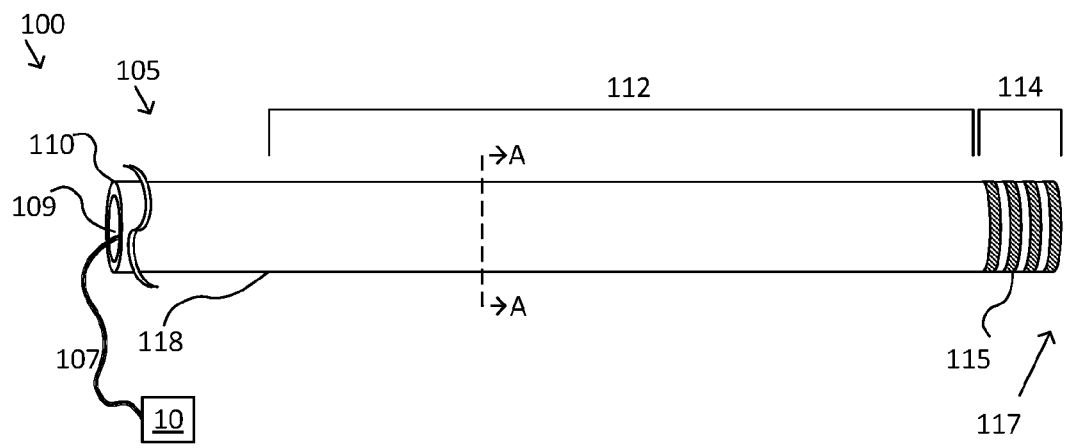
FIG. 1 illustrates an example of an embodiment of a medical apparatus including a lead device.

Various embodiments include a medical treatment apparatus including protruding anchoring mechanisms to anchor a portion of the apparatus in tissue.

In one or more embodiments of a medical treatment application or process, a medical treatment apparatus can include, for example, a cord, catheter, lead or other device (for convenience hereinafter, referred to as a lead device) which can be introduced into an animalia body, such that a treatment portion of the lead device is positioned at a target location within the body. A few examples of target locations are proximate the spinal cord, heart, stomach, or bladder, or proximate a nerve or muscle. The introduction of the lead device can be performed by a doctor or medical professional, often through the use of an imaging modality (e.g., fluoroscopy, ultrasound, endoscopic image capture, or other imaging technique) or sensing devices that allow attending personnel to position the treatment section of the lead device relatively precisely at the target location. In one or more embodiments, the implantation process may involve use of a separate implantation device (e.g., an introducer) which can provide a conduit or path for the lead device as it is introduced. Once the lead device is positioned at the target location, the implantation device can be removed. It may then be desirable for the lead device to retain its position for days, weeks, months or years with little movement, to improve eventual success of the treatment being applied.

As an example of an embodiment of a medical treatment application or process, a lead device may be implanted alongside a nerve to provide electrical stimulation to the nerve, (e.g., for pain management, or for blocking of signal conduction along the nerve to avoid a responsive action by the body, or to activate signal conduction in the nerve), or alongside a muscle (e.g., to allow or to inhibit muscle contraction), or at other sites. Implantation may be performed, for example, by using an introducer to deliver the lead device, and removing the introducer once the lead device is positioned, thereby allowing anchoring mechanisms of the lead device to deploy. In one or more embodiments, a stimulation controller in electrical communication with the lead device may provide energy for, and control, electrical stimulation provided by the lead device.

While the static positioning of lead devices in tissue can be important for the effectiveness of the respective treatment, the dynamic nature of a living body can make effective anchoring of such lead devices challenging. A common challenge with implanted lead devices is movement, where the lead device is moved after being positioned at the target location by body movement, by external forces being applied to the body, or by external forces being applied to a controller connected to the lead device which forces propagate to the lead device. An anchoring mechanism can be desirable to resist such movement of the lead device.

Discussed below are embodiments of anchoring mechanisms that resist movement, such as resisting movement of a lead device or another apparatus on which the anchoring mechanism is attached, disposed, affixed, connected, formed, or otherwise incorporated (any such relationship hereinafter referred to for convenience as incorporated). For convenience, resistance to movement is discussed hereafter in terms of resistance to axial movement or migration of a lead device. It is to be understood, however, that the anchoring mechanisms contemplated by this disclosure resist other forms of movement as well, and are applicable to apparatuses other than lead devices.

Axial migration may be retrograde or antegrade. Retrograde migration refers to axial movement of a lead device away from a target treatment location, while antegrade migration refers to axial movement towards the target location. Either type of migration can reduce effectiveness of the medical treatment being provided. Various factors can contribute to forces that cause such migration. These include, for example, the reaction of tissue in the body (e.g., settlement of tissue, formation of scar tissue) to the presence or movement of the lead device, as well as body movement and typical dynamic fluctuations within a body.

To minimize lead device migration, one or more anchoring mechanisms may be incorporated with or on the lead device to anchor the lead device within body tissue. When implanted, the anchoring mechanism resists migration of the lead device in at least one or both axial directions.

In various embodiments, the lead device may include an arrangement of anchoring mechanisms, where the arrangement includes a first set of anchoring mechanisms having a first axial orientation, and a second set of anchoring mechanisms having a second axial orientation.

In one or more embodiments, a medical treatment apparatus is operated by advancing an introducer into a body, where the introducer includes a lumen that retains a lead device, and the lead device includes a shaft with protruding anchoring mechanisms. When retained by the lumen, the individual anchoring mechanisms are forced inwards, so as to be under bias. Using the introducer, the lead device is advanced until the lead device reaches a target region within the body. When the lead device reaches the target region, the introducer may be removed to allow the anchoring mechanisms to release outward into an unbiased state.

In embodiments, a lead device is provided for a medical device that includes a lead shaft and at least one anchoring mechanism. Each anchoring mechanism is disposed over the lead shaft, such that the lead shaft is positioned within an opening defined by the anchoring mechanism. In embodiments, each anchoring mechanism corresponds to one of a notched anchor (or anchor structure), a wire structure or a ring structure.

In other embodiments, the lead device includes multiple anchoring mechanisms, including (i) a first anchoring mechanism that is one of a notched anchor, a wire structure, and or a ring structure, and (ii) a second anchoring mechanism that is a different one of the notched anchor, the wire structure or the ring structure as compared to the first anchoring mechanism. By way of example, the first anchoring mechanism may correspond to a notched anchor, and the second anchoring mechanism may correspond to a wire structure or ring structure. Different types of anchoring mechanisms (e.g., notched anchor, wire structure, or ring structure) are described with examples provided below.

As used herein, term such as "about" and "substantially" (and variants thereof) means within 20% of a referenced quantity.

FIG. 1 illustrates a medical apparatus 100 including an optional controller 10 and a lead device 105 including a lead shaft 110 having a channel 109 (lumen) extending therethrough. The lead device 105 in the embodiment of FIG. 1 includes a fixation region 112 and a treatment region 114 which incorporates one or more electrodes 115 (four are shown) at a distal end 117 of the lead shaft 110. In other embodiments, the fixation region 112 and/or the treatment region 114 may be at different locations along the lead shaft 110, and/or there may be multiple instances of the fixation region 112 for fixation at different locations along the lead shaft 110, and/or there may be multiple instances of the treatment region 114 for applying treatment from different locations along the lead shaft 110. For example, multiple electrodes 115 may be positioned along the lead shaft 110, with one or more treatment regions 114 interspersed between the electrodes 115 or between sets of the electrodes 115, where a number of electrodes in a set may be equal or different than a number of electrodes in another set.

In an embodiment, the lead shaft 110 has a diameter in a range of about 0.03 inches to about 0.04 inches (e.g., equal to or less than 1 millimeter (mm)).

Controller 10 may be in electrical communication with the electrode(s) 115 to provide energy to the electrode(s) 115 in a controlled fashion. For example, the controller 10 may be used to provide and control energy for electrical stimulation treatment, such as to nerve endings, muscles, or organs. In embodiments including the optional controller 10, a conductor 107 (e.g., a wire or multiple wires, or a printed pattern, or other electrical/signal connection) may extend from the controller 10 through channel 109 of the lead shaft 110 to the electrode(s) 115, to activate the electrode(s) 115 in accordance with a treatment plan.

The lead shaft 110 can be introduced at a position and to a depth where the electrode(s) 115 are sufficiently proximate to a target region where stimulation is to be provided as treatment. For at least some treatments (e.g., treatments that include stimulation of nerves), precision placement of the electrode can be important for the treatment to be effective, and migration of the lead shaft 110 can result in reduced effectiveness of the treatment, or inadvertent effects.

The lead shaft 110 includes a perimeter shell 118. In one or more embodiments, a portion of the perimeter shell 118 may be formed separately from a remainder of the lead shaft 110 of the lead device 105. In one or more embodiments, a portion of the perimeter shell 118 can correspond to a thickness that is unitarily formed or otherwise integrated with the lead shaft 110. For example, portions of the perimeter shell 118 can be provided using a sleeve, where the sleeve is wrapped, fitted or otherwise formed over the lead shaft 110; and/or portions of the perimeter shell 118 can be formed as part of unibody lumen structure of the lead shaft 110. The fixation region(s) 112 are incorporated into the perimeter shell 118.

To minimize lead device migration, one or more anchoring mechanisms may be incorporated with or on the lead device to anchor the lead device within body tissue. When implanted, an anchoring mechanism resists migration of the lead device in at least one or both axial directions.

Figure 2:
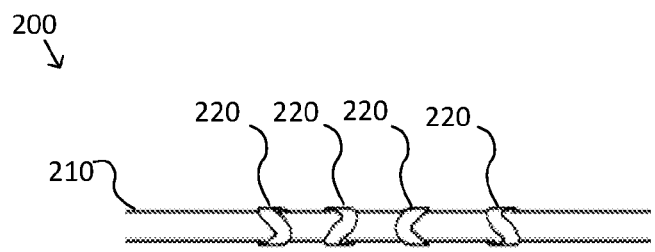
FIG. 2 illustrates an example of embodiments of notched anchors disposed on a lead shaft.

FIG. 2 illustrates an example of an embodiment of a lead device 200 including a lead shaft 210 and multiple notched anchors 220 to anchor the lead shaft 110 in tissue (e.g., animalia tissue).

FIG. 3A—FIG. 3D illustrate a notched anchor 300, according to one or more embodiments. The notched anchor 300 may be implemented in accordance with any of the examples described herein, including with embodiments of FIG. 1 and FIG. 2.

Figure 3A:
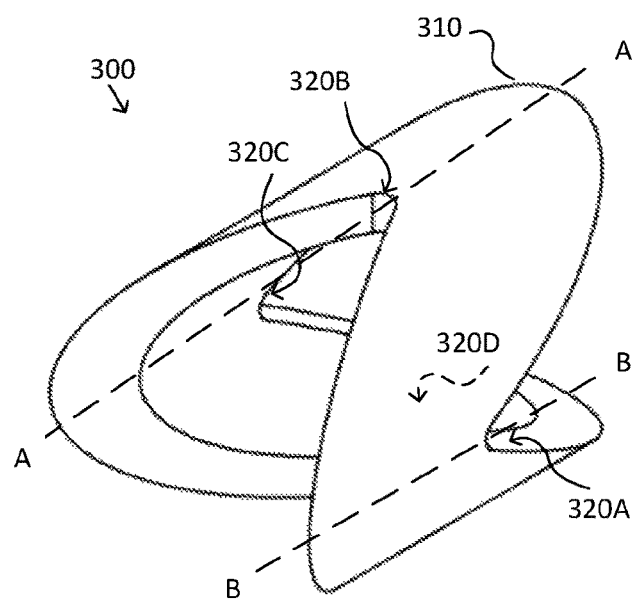
FIG. 3A, FIG. 3B, FIG. 3C, and FIG. 3D illustrate an example of an embodiment of a notched anchor.

FIG. 3A illustrates a perspective view of the notched anchor 300. In one or more embodiments, the notched anchor 300 includes a perimeter shell 310 including one or more notched formations 320 (e.g., notched formations 320A, 320B, 320C, 320D, where notched formation 320D is not visible in this view). The notched formations 320 may be V-shaped. In other variations, the notched formations 320 may be rounded (e.g., U-shaped).

In one or more embodiments, the notched formations 320 may be provided in pairs in which one notched formation 320 is opposite the other notched formation 320 on the perimeter shell 310, such as illustrated by the relationship between notched formations 320A, 320C. In one or more embodiments, one notched formation 320 in a pair is diametrically aligned and radially offset from the other notched formation 320 in a pair, such as illustrated by the relationship between notched formations 320A, 320B. For example, two notched formations 320 in a pair may be radially offset by 90 degrees.

In one or more embodiments, the notched anchor 300 includes two pairs of notched formations 320 in which one pair of notched formations 320 is diametrically aligned and radially offset from the other pair of notched formations 320, such as illustrated by the relationship between the pair of notched formations 320A, 320C and the pair of notched formations 320B, 320D. For example, two pairs of notched formations 320 may be radially offset by 90 degrees.

The structure of the notched anchor 300 includes an interior space or opening 301 (see FIG. 3D) for attaching the notched anchor 300 to a lead shaft of a lead device (e.g., lead shaft 110 of FIG. 1).

Figure 3B:
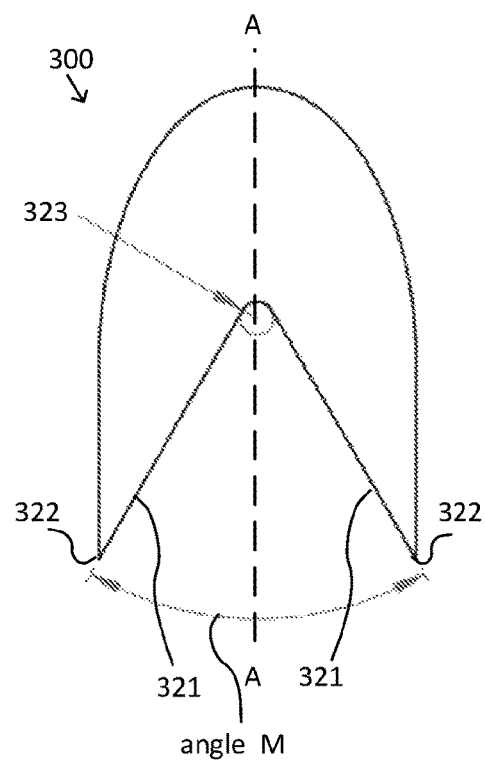

FIG. 3B illustrates a two-dimensional view of the notched anchor 300, in an orientation such that line A-A shown in FIG. 3A is approximately vertical in FIG. 3B. In the particular viewpoint illustrated in FIG. 3B, the pair of notched formations 320B, 320D are shown to be aligned, with each of the notched formations being defined by a pair of slanted lengths 321 that extend from a respective perimeter point 322 inward to a juncture 323. Two other notched formations (320A, 320C) are not visible in the particular viewpoint illustrated in FIG. 3B. An angle M formed by the opposing slanted lengths 321 may range between, for example, 30-75 degrees. In the example shown, the angle M between the slanted lengths 321 is approximately 60 degrees.

Figure 3C:
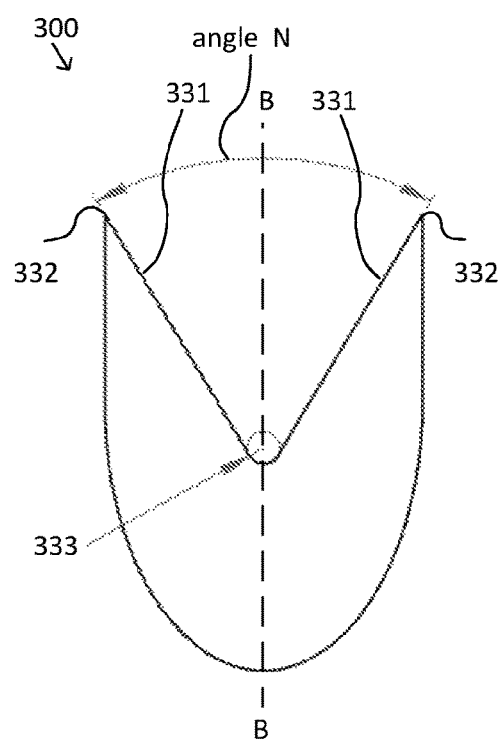

FIG. 3C illustrates another two-dimensional view of the notched anchor 300, in an orientation such that line B-B shown in FIG. 3A is approximately vertical in FIG. 3C. FIG. 3C illustrates a viewpoint that represents approximately a 90-degree rotation of the view illustrated in FIG. 3B. The side view depicts two notched formations 320A, 320C provided on the notched anchor 300. Like the notched formations 320B, 320D shown in FIG. 3B, the notched formations 320A, 320C as viewed in the viewpoint provided in FIG. 3C, are aligned and are defined by a pair of slanted lengths 331 that extend from respective perimeter points 3326 inward to a juncture 333. Two other notched formations (320B, 320D) are not visible in the particular viewpoint illustrated in FIG. 3C. An angle N formed by the opposing slanted lengths 331 may range between, for example, 30-75 degrees. In the example shown, the angle N between the slanted lengths 331 is approximately 60 degrees.

According to one or more embodiments, the notched formations 320A, 320B, 320C, 320D may be similar to each other. In other words, the angle M formed by the opposing slanted lengths 321 may be approximately the same as the angle N formed by opposing slanted lengths 331. Similarly, the radius of curvature of juncture 333 may be the same or substantially the same as the radius of curvature of juncture 323. In other implementations, the aforementioned angles and radiuses of curvature may be varied between instances of notched formations 320. In an embodiment, the characteristic radius of curvature of the juncture 323 and/or the juncture 333 is about 0.0035 inches (or about 0.089 mm). Based on implementation, the characteristic radius of curvature may be more or less.

Each pair of notched formations 320 (e.g., the pair of notched formations 320A, 320C or the pair of notched formations 320B, 320D) may resist migrational forces of a particular axial direction. In particular, when a lead device including the notched anchor 300 is introduced into tissue and the introducer is removed, the void region of each notched formation 320 (the region between the slanted lengths forming the notched formation 320, to a thickness of the perimeter shell 310) may receive and engage tissue. As a result, the notched anchor 300 may resist forces that would tend to cause the lead device to move axially in a direction tending to cause further tissue engagement within the void. In this manner, the inclusion of notched formations 320 in opposite orientations allows for the notched anchor 300 to resist migrational forces in either axial direction. Further, for similar reasons, the inclusion of notched formations 320 in general allows for rotational resistance (e.g., circumferentially around a central axis of the lead device).

Figure 3D:
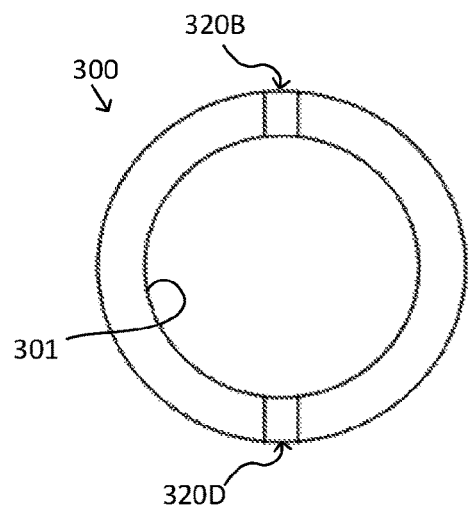

FIG. 3D illustrates an axial view of the notched anchor 300 in which the notched formations 320B, 320D are visible. The notched anchor 300 includes the opening 301 that may be dimensioned to receive a lead shaft. In one or more embodiments, the lead shaft may be press-fitted within the opening 301, to affix the notched anchor 300 to the lead shaft. In other embodiments, adhesives or other coupling mechanisms may be used to affix the notched anchor 300 to the lead shaft that is received within the opening 301.

Figure 4A:
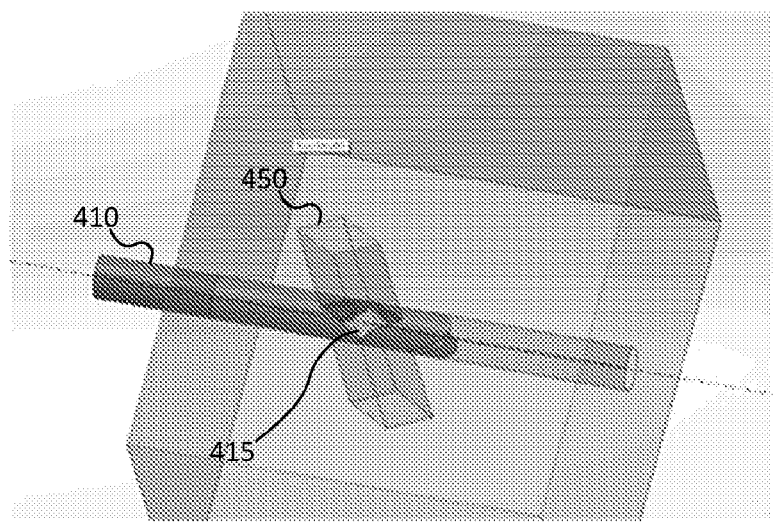
FIG. 4A and FIG. 4B illustrate an example of an embodiment of forming notched anchors.
Figure 4B:
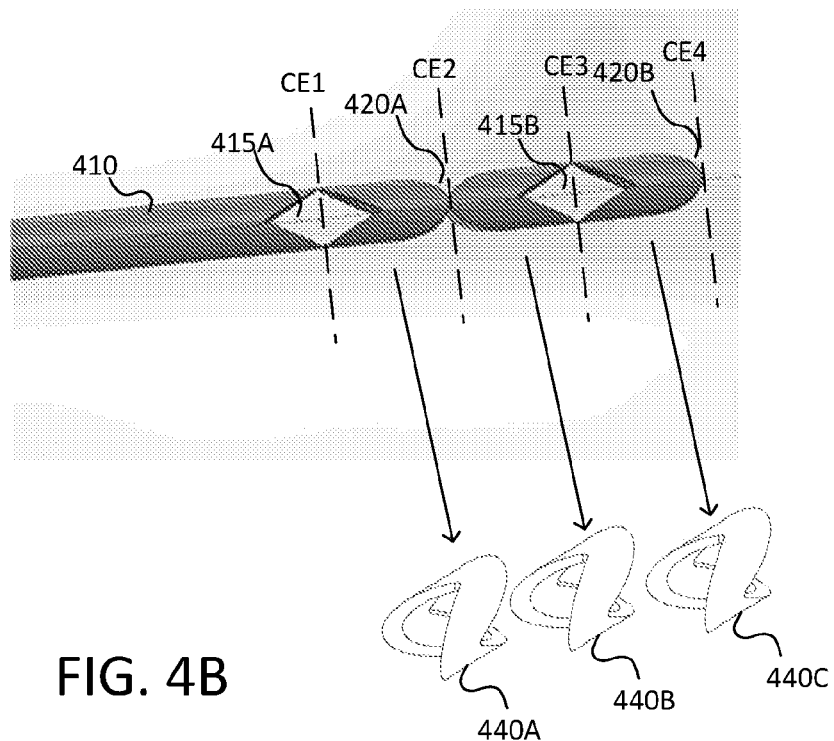

FIG. 4A and FIG. 4B illustrate an example of an embodiment of a process to form a notched anchor having notched formations (e.g., notched formations 320).

In one or more embodiments, a tubular length 410 of sheath material may be formed from polymeric material, such as 65D polyurethane or 75D polyurethane. The tubular length 410 may be positioned to have a first radial orientation. While the tubular length 410 is in the first radial position, a first pair of voids 415 may be formed in the tubular length 410. For example, a void shape of diamond, rhombus or other polygonal shape may be punched through the tubular length 410 (e.g., using a punching component 450), such that the voids 415 are formed as a pair on opposite sides of the tubular length. In this way, each void 415 of the pair is formed to be diametrically aligned.

The tubular length 410 may be advanced by one notched anchor length while being radially rotated by 90 degrees, then subjected to a void formation process where a second pair of voids 420 are formed in the tubular length 410. The second pair of voids 420 may have a similar or substantially identical shape as the first pair of voids 415, or the second pair of voids 420 may have a different shape than the first pair of voids 415.

A centerline (CE) of each pair of voids 415, 420 may delineate an end of a notched anchor. For example, with respect to voids 415 shown in FIG. 4B as voids 415A, 415B and voids 420 shown in FIG. 4B as voids 420A, 420B: a centerline CE1 through void 415A and a centerline CE2 through void 420A together define a notched anchor 440A; the centerline CE2 through void 420Aa and a centerline CE3 through void 415B together define a notched anchor 440B; and the centerline CE3 through void 415B and a centerline CE4 through void 420B together define a notched anchor 440C. The notched anchors 440A, 440B, 440C (and other notched anchors formed by introducing voids into tubular length 410) can be separated from the remainder of the tubular length 410. A number of voids may be formed in the tubular length 410 as needed to form a desired quantity of notched anchors. Although voids 415, 420 are illustrated as being formed approximately 90 degrees rotationally from each other, voids may be formed at any rotational angle along tubular length 410 to form a variety of shapes of notched anchors.

The notched anchors 440 may then be affixed to a lead shaft of a lead device. According to one or more embodiments, the lead shaft may be received in an opening of the notched anchor. The lead shaft may be press-fitted within the opening of the notched anchor. For example, the lead shaft may be formed from polymeric material similar to the material used to form the notched anchor. In one or more embodiments, one of the lead shaft or notched anchor is formed from polymeric material that has a hardness which is greater than the hardness of the polymeric material used to form the other of the notched anchor or lead shaft. For example, the lead shaft may be formed from polyurethane 55 D while the notched anchor is formed from 65 D polyurethane or 75 D polyurethane. The material composition of the respective components allows for the lead shaft to be press-fitted to the notched anchor. In other variations, the notched anchors may be adhered to the lead shaft using adhesives or other types of coupling mechanisms.

In one or more embodiments, a single void 415 may be formed on one side of the tubular length 410 rather than on both sides. Accordingly, a notched anchor 440 may have a pattern of cutouts along the perimeter shell.

FIG. 5 illustrates a method for forming a notched anchor, in accordance with one or more embodiments. A method such as described with FIG. 5 may be used to create a notched anchor such as described with respect to any of the embodiments of FIG. 2, FIGS. 3A-3D or FIGS. 4A-4B. In describing an example of FIG. 5, reference may be made to FIG. 4A and FIG. 4B by way of illustration of an example device, structure or component.

At 510, a tubular length (e.g., tubular length 410) is positioned in a first radial orientation. A first pair of voids (e.g., voids 415) is formed in the tubular length. The voids in the first pair of voids are diametrically aligned.

At 520, the tubular length is positioned in a second radial orientation. A second pair of voids (e.g., voids 420) is formed in the tubular length. The voids in the second pair of voids are diametrically aligned.

At 530, one or more notched anchors (e.g., notched anchors 440) are separated from the tubular length, at approximately center lines of the first pair of voids and the second set of voids (e.g., as described with respect to separating notched anchors 440A, 440B, 440C from tubular length 410 in FIG. 4B).

At 540, one or more notched anchors (e.g., notched anchors 440) are affixed to a lead shaft (e.g., similar to the notched anchors 220 on lead shaft 210).

Notched anchors such as described with respect to FIG. 2, FIGS. 3A-3D, and FIGS. 4A-4B provide examples of embodiments of one type of anchoring mechanism for a lead device. Other types of anchoring mechanisms are described next.

FIG. 6, FIGS. 7A-7D, and FIGS. 8A-8B illustrate examples of embodiments of a wire structure anchor.

Figure 6:
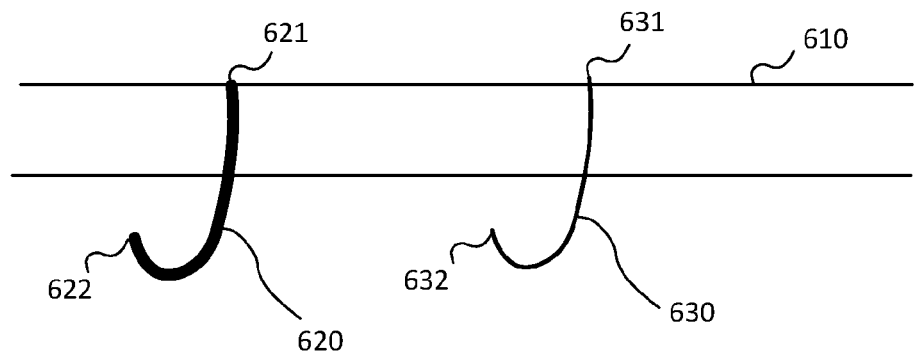
FIG. 6 illustrates an example of embodiments of wire structures.

FIG. 6 illustrates a lead shaft 610. A wire structure 620 and a wire structure 630 are affixed to lead shaft 610. The wire structure 620 includes a base 621 contacting lead shaft 610 and a flaring segment 622. The flaring segment 622 extends away from the lead shaft 610.

The flaring segment 622 may have a characteristic flexibility, to allow the flaring segment 622 to move inward towards the lead shaft 610. The flexibility of the flaring segment 622 can be based on parameters such as the thickness and length of the respective wire segment, as well as the material from which the flaring segment 622 is formed. The flexibility of the flaring segment 622 may also be based on the respective shape formed by the respective wire segment when in the expanded state.

In one or more embodiments, the base 621 can include one or more coils that are provided over the lead shaft 610. In variations, the base 621 may include a plate, segment or wire length that is permanently affixed to the lead shaft 610, such as through welding, adhesives, or manufacturing process (e.g., three-dimensional printing). In other variations, the base 621 can be securely coupled to the lead shaft 610 through use of a coupling mechanism.

In one or more embodiments, the flaring segment 622 is a continuous extension of the base 621. For example, a wire of a given length can be wrapped around the lead shaft to form one or more coils from which the flaring segment 622 can be extended as a unitary extension. In one or more embodiments, the flaring segment 622 is a separate component, affixed to the base 621.

The wire structure 630 includes a base 631 and a flaring segment 632. The wire structure 630 is similar to the wire structure 620, with a difference being that a diameter of material used in the wire structure 630 is smaller than a diameter of material used in the wire structure 620, indicating that material forming a wire structure (e.g., wire structure 620 or wire structure 630) may be selected, for example, for an intended placement site in the body, an intended form of manufacture, and intended placement tool, or other consideration.

Figure 7A:
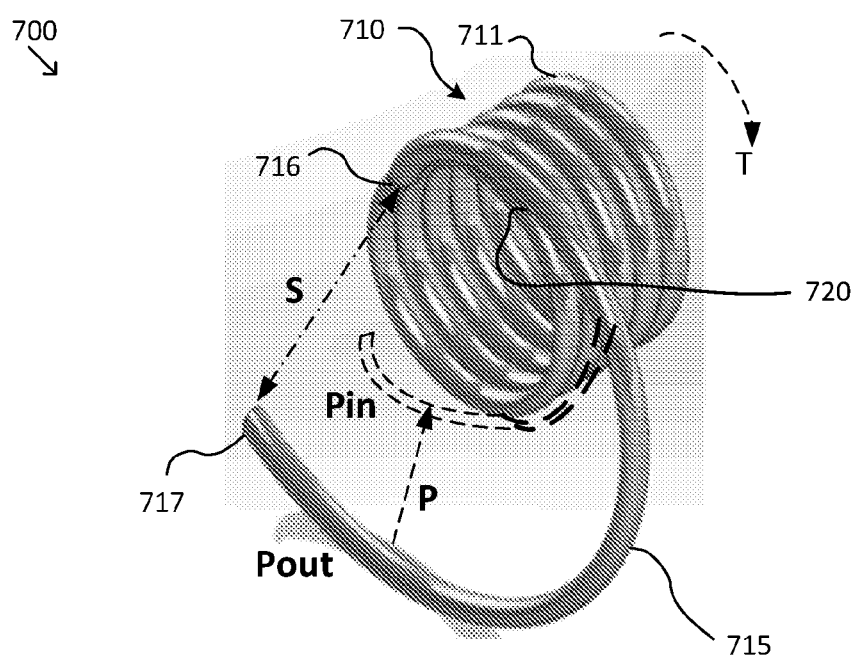
FIG. 7A illustrates an example of an embodiment of a wire structure.

FIG. 7A illustrates a wire structure 700 (e.g., an embodiment of the wire structure 620 or the wire structure 630) having a coiled base structure 710. In one or more embodiments, the wire structure 700 includes a flaring segment 715 that extends from or is otherwise connected to the coiled base structure 710, and the coiled base structure 710 is dimensioned and/or structured to receive a portion of a lead device (e.g., lead shaft 610).

The coiled base structure 710 may include one or more coils 711. The coils 711 may be aligned and dimensioned to define (e.g., dimension and shape) an opening 720 to receive the lead shaft. In one or more embodiments, the coils 711 may be dimensioned such that the lead shaft can be press-fitted through the opening 720 to a desired axial position. As an addition or variation, a portion of the lead device can be bonded, adhered or fastened to the wire structure 700 via the opening 720.

While the embodiment of FIG. 7A illustrates the use of coils for use as a base structure, in other embodiments, the flaring segment 715 can be extended or otherwise connected to another type of base structure, such as a rounded metal plate that can secure to an exterior surface of the lead shaft.

The flaring segment 715 may extend from one of the coils 711 of the coiled base structure 710 to define at least a partially shaped area or volume in the region that surrounds the individual coils 711. By way of example, the flaring segment 715 may extend outward in the form of a helix, corkscrew or other spiral structure (e.g., pig-tail). In one or more embodiments, the flaring segment 715 may form a unitary extension of one of the coils 711. In other embodiments, the flaring segment 715 may be joined or otherwise attached to one of the coils 711, such as through welding or adhesives.

According to one or more embodiments, the flaring segment 715 may be said to extend between a stem 716 and a distal tip 717, with the stem 716 coinciding with a section of the flaring segment 715 that is attached to or extends into one of the coils 711 of the coiled base structure. In one or more embodiments, the flaring segment 715 spirals outward from the coiled base structure 710, with the distal tip 717 of the flaring segment 715 extending between about 180 to 270 degrees of a full loop in relation to its stem 716. In variations, the distal tip 717 may extend less than 180 degrees (e.g., between 30 degrees and 120 degrees) or more than 270 degrees (e.g., between 270 and 360 degrees) in relation to its stem 716. As an addition or variation, in other embodiments, the flaring segment 715 can extend longitudinally while forming the partial or full loop about its stem 716. In other variations, the flaring segment 715 can form more than one loop about the base thickness while at the same time extending longitudinally, so as to extend, for example, a helix, corkscrew or spiral shape about a portion of a lead shaft.

In one or more embodiments, a cross-sectional dimension of the partial or full loop formed by the flaring segment 715 may range between about 0.06 inches (0.16 centimeters) and 0.2 inches (0.50 centimeters). The dimension and shape of the area defined by the flaring segment 715 may provide for a separation distance as between a section of the flaring segment 715 and a closest point of the lead shaft, meaning that the flaring segment 715 can, upon introduction of a corresponding lead shaft, extend into tissue that surrounds the lead shaft, thereby anchoring the lead shaft. The length of the flaring segment 715 may vary to accommodate a desired separation distance as between its distal tip 717 and stem 716. The length of the flaring segment 715 may also vary to accommodate a desired shape that is formed by the flaring segment 715 when extended. In one or more embodiments, the flaring segment 715 is rounded, so as to form a partial circle or ellipse about the lead shaft when the flaring segment 715 is in the extended state. Thus, in the extended state, the flaring segment 715 can form, for example, a quarter-circle, half-circle, three-quarters circle or other rounded partial or full loop shape. In one or more embodiments, a length of the wire that forms the flaring segment 715 may be selected such that a maximum span (S) of any portion of the flaring segment 715 with respect to the stem 716 ranges between a maximum value that is greater than 0.2 inches (or greater than 0.5 centimeters) and a minimum value that is less than 0.06 inches (or less than 0.16 centimeters). In other embodiments, the flaring segment 715 may be dimensioned and shaped to form more than one loop or revolution about a point of reference defined by the stem 716 (e.g., to form a spiraling helix or 'pig-tail'). In one or more embodiments, the length of the flaring segment 715 may be based on a desired shape and/or a maximum span of the flaring segment 715 with respect to the stem 716 when the flaring segment 715 is in the expanded state, subject to a constraint of the flaring segment 715 being appropriately dimensioned to allow for contraction and encapsulation of an attached lead device by an introduction device. Additionally, the shape and/or dimension of the flaring segment 715 may be selected by factors such as the nature of the surrounding tissue.

In the embodiment of FIG. 7A, an expanded and contracted position for the flaring segment 715 is illustrated by Pin (contracted position) and Pout (expanded position). The difference in position of individual points of the flaring segment 715 between the expanded and contracted states may be collectively represented by (P). In some variations, different points of the flaring segment 715 may move different amounts to reach the respective position of the contracted state. In some variations, the flaring segment 715 is sufficiently flexible to allow for the flaring segment 715 to bend around obstacles such as bone or cartilage.

In one or more embodiments, the flaring segment 715 has a material composition and thickness that allows for the flaring segment 715 to contract under bias so that the flaring segment 715 may abut or touch an exterior of a lead shaft at one or more points. The material composition and thickness of the flaring segment 715 may further allow for the flaring segment 715 to release from the contracted position into the expanded position. In the contracted state, the flaring segment 715 may be forced inward to allow for the lead shaft to be encapsulated within an introduction device for advancement into the patient's tissue. Once the lead shaft is introduced and the introduction device is removed, the flaring segment 715 can release into the expanded state. Accordingly, the flaring segment 715 may be structured by dimension (e.g., thickness) and composition (e.g., material stiffness or characteristic flexibility) so that the flaring segment 715 allows for encapsulation by the introduction device, as well as subsequent release from the contracted position into the expanded state in conjunction with removal of the introduction device. According to one or more embodiments, a thickness of the flaring segment 715 can range between 0.008 inches (0.02 centimeters) and 0.01 inches (0.025 centimeters). In variations, the thickness may be greater than 0.01 inches (0.025 centimeters) or less than 0.008 inches (0.02 centimeters).

Although illustrated as having arcuate coils 711 defining a substantially cylindrical opening 720, the coiled base structure 710 may define other shapes of opening 720.

Optionally, the lead shaft may be turned upon introduction to a patient, where the turn to the wire structure 700 is represented by (T). In one or more embodiments, once the lead shaft is introduced into the patient with an electrode (e.g., the electrode 115 of FIG. 1) positioned at the target region, the flaring segment 715 may release into the expanded position. Subsequently, the lead shaft may be turned while in the expanded state to cause the wire structure 700 to also turn by a corresponding amount. When turned, the flaring segment 715 may engage tissue or other biological mass of the patient's body, with the distal tip 717 forming a loop or other rounded area about the stem 716 of the flaring segment 715. To illustrate one or more embodiments, the lead shaft may be turned by, for example, a quarter-turn to cause the distal tip 717 to travel a corresponding arc length from an original position to a first turned position. In variations, the degree of the turn applied to the lead shaft may vary. For example, the lead shaft may be turned a half-turn to cause the distal tip 717 to travel an equivalent arc length to a second turned position. The amount of turn, if any, which the lead shaft may undergo may thus vary by design, implementation and/or application.

In some variations, the wire structure 700 may include one or more structural features to facilitate the flaring segment 715 to rotate in the patient's tissue. For example, in one or more embodiments, the distal tip 717 may be shaped as a point to enable the flaring segment 715 to penetrate through surrounding tissue when the lead shaft is turned.

Figure 7B:
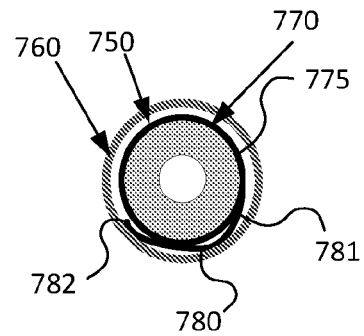
FIG. 7B, FIG. 7C, and FIG. 7D illustrate examples of embodiments of wire structures.

FIG. 7B is a cross-sectional view of a lead device 750 that is contained within an introduction device 760. In FIG. 7B, the introduction device 760 advances the lead device 750 through the tissue of a patient to reach a target region. Introduction device 760, also referred to as an introducer, may correspond to one or more of a catheter, guiding catheter, trocar, surgical port (including minimally invasive surgical port) or the like. The lead device 750 may include one or more wire structures 770 (e.g., wire structures 620, 630, 700) to anchor the lead device 750 within the body. In the embodiment shown, the wire structures 770 include at least one flaring segment 780 that is constructed in accordance with any of the embodiments described elsewhere in this document with respect to flaring segments. In the embodiment of FIG. 7B, the flaring segment 780 extends from a coil of a coiled base structure 775. The flaring segment 780 includes a stem 781 that connects or extends into one of the coils of the coiled base structure 775, as well as a distal tip 782. When the lead device 750 is enclosed by the introduction device 760, the flaring segment 780 may be contracted inward under bias to allow for containment within a lumen of the introduction device 760. The inner walls of the introduction device 760 which define the lumen may contact the flaring segment 780 at one or multiple points along the length of the flaring segment 780, so as to bias the flaring segment 780 against the lead device 750, to reduce the overall radial span of the flaring segment 780 during introduction into the body.

Figure 7C:
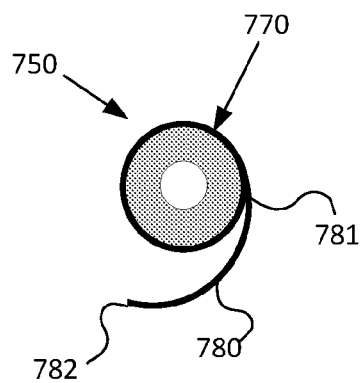

FIG. 7C is a cross-sectional view of the lead device 750 positioned within the body, with the introduction device 760 removed. As shown, once the introduction device 760 advances an electrode of the lead device 750 to a target region, the introduction device 760 may be removed. With the introduction device 760 removed, the flaring segment 780 releases from the contracted state into an expanded state. Subsequently to the introduction device 760 being removed, tissue surrounding the lead device 750 can settle or otherwise adjust, and over time, scarring may form around the lead device 750 and the wire structure 770 (including the flaring segment 780). The settlement of tissue and the formation of scar tissue can form barriers for the wire structure 770 against which lead migration can be resisted. Additionally, the flaring segment 780 can resist migration to an extent when initially deployed. Treatment may be provided to the target region using the electrode, which may communicate with a controller or medical apparatus via communication conductors (e.g., wires) running through a lumen of the lead device 750.

Figure 7D:
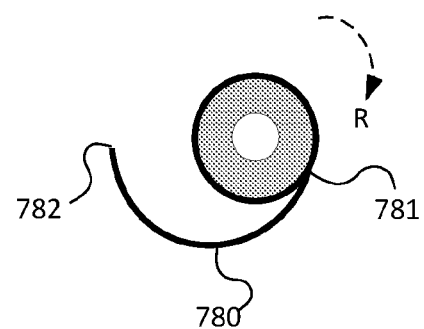

FIG. 7D is a cross-sectional view of the lead device 750 after being subjected to a turn. In one or more embodiments, lead device 750 is turned (as represented by R) causing the flaring segment 780 to also turn with the lead device 750. The degree of the turn may vary according to factors such as the location of the target region in the body and the number of wire segments which are provided on the lead device. In one or more embodiments, the lead device 750 is turned by an amount that may range between 90 and 270 degrees. In other embodiments, the lead device 750 is turned by a lesser amount, such as between 30 and 90 degrees, or by a greater amount, such as between 270 and 360 degrees. Still further, in other embodiments, the lead device 750 may be turned by more than one revolution, including multiple revolutions.

In one or more embodiments, the lead device 750 is turned upon the introduction device 760 being removed, such that the wire structure 770 is turned before tissue settlement and/or scarring occurs. In one or more embodiments, the lead device 750 is turned a subsequent time interval following the introduction device 760 being removed, such that the wire structure 770 engages tissue from settlement and/or scarring when turned. Still further, in one or more other embodiments, the lead device 750 may be turned at multiple times during an interval of treatment of the patient. The lead device 750 may not be intentionally turned at all, allowing for tissue growth around flaring segment 780 over time; flaring segment 780 may provide resistance to movement axially and radially in its initial position.

Figure 8A:
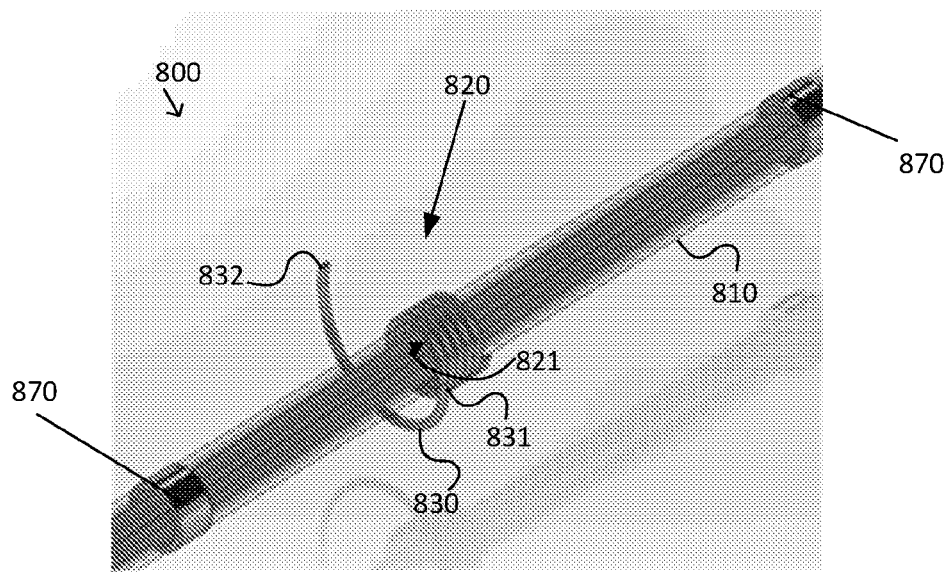
FIG. 8A and FIG. 8B illustrate examples of embodiments of wire structures.

FIG. 8A illustrates an embodiment of a wire structure 820 affixed to a lead shaft 810 of a lead device 800. As shown, the lead shaft 810 of the lead device 800 is received in an opening 821 defined by the wire structure 820. A coiled base structure 825 includes six (6) coils that wrap around the lead shaft 810. The wire structure 820 includes a flaring segment 830 extending from a stem 831 contacting the coiled base structure 825 to a distal tip 832, forming a partial loop (e.g., half-loop) about the lead shaft 810. The partial loop formed by the flaring segment 830 is extended outward from the lead shaft 810 in a spiral or circuitous manner. When the lead device 800 is implanted in tissue, the flaring segment can extend outward a sufficient distance to engage tissue which may have not displaced as a result of the advancement of the introduction device. By engaging tissue that has been subjected to less displacement (as a result of the introduction device), the wire structure 820 is able to initially anchor the lead device 800.

Figure 8B:
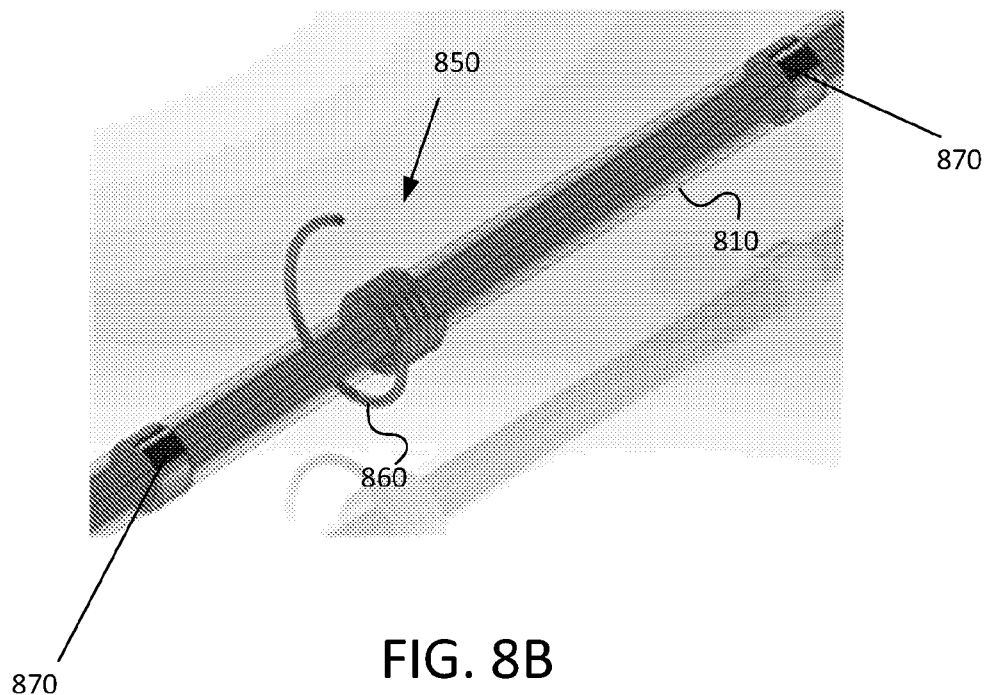

FIG. 8B illustrates a variation similar to wire structure 820 in FIG. 8A, with a difference being that a wire structure 850 includes a flaring segment 860 that forms a three-quarter partial loop about the lead shaft 810. As compared to the embodiment of FIG. 8A, the additional length of the flaring segment 860 allows for the wire segment 850 to engage a greater volume of surrounding tissue, thereby allowing the wire structure 850 to provide more resistance against migrational forces.

FIG. 8A and FIG. 8B further illustrate components 870. In an embodiment, the lead device 800 includes one or more components 870. In an embodiment, a component 870 is an electrode. In an embodiment, a component 870 is a locational marker for an imagining modality.

FIG. 9A-FIG. 9G illustrate embodiments of another type of anchoring mechanism, in the form of a ring structure.

Figure 9A:
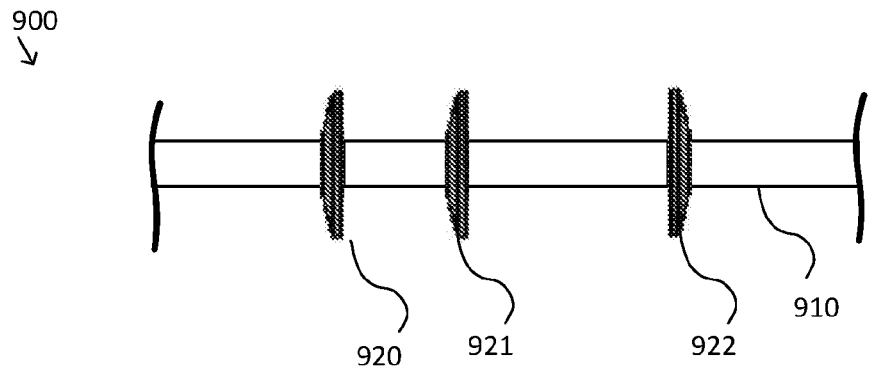
FIG. 9A illustrates an example of embodiments of ring structures disposed on a lead shaft.

FIG. 9A illustrates a lead device 900 incorporating multiple ring structures along a lead shaft 910. While FIG. 9A illustrates three ring structures 920, 921, 922, in variations, there may be more of fewer ring structures to provide a desired level of resistance to either retrograde or antegrade migration. As illustrated by FIG. 9A, the lead device 900 is shown to have incorporated two ring structures 920, 921 oriented to resist retrograde migration, and the ring structure 922 oriented to resist antegrade migration.

The structural characteristics of the individual ring structures 920, 921, 922 may be varied to provide different levels of stiffness or flexibility. The determination of the number of ring structures (e.g., ring structures 920, 921, 922) to deploy, the respective orientation of the individual ring structures, as well as a desired amount of flexibility or stiffness from each ring structure, can be based on a variety of considerations, including: (i) the type of medical treatment (e.g., a need for precision placement of the lead device 900), (ii) a length of time the treatment is to be applied, (iii) a type of tissue in which the lead shaft 910 is to reside, and/or (iv) a depth of penetration for a distal tip of the lead device 900.

Figure 9B:
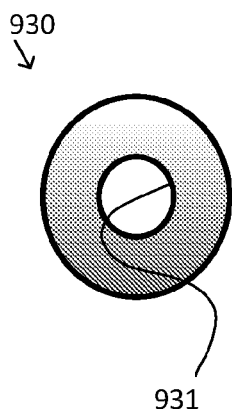
FIG. 9B, FIG. 9C, and FIG. 9D illustrate examples of embodiments of ring structures.

FIG. 9B illustrates an annular ring structure 930, illustrating that a ring structure (e.g., any of ring structures 920, 921, 922) can be shaped as a ring or disk, having an elliptical (e.g., circular) perimeter. The ring structure 930 in the embodiment of FIG. 9B defines an opening 931 in its mid-region to receive the lead shaft. In some examples, the ring structure 930 deforms at the opening 931 when receiving the lead shaft. The deformation can cause the ring structure 930 to increase grip on the lead shaft, further adding to the adhesion of the ring structure 930 to the lead shaft. In some examples, the ring structure 930 is formed from deformable material, such as polymeric material (e.g., silicone elastomer, polyurethane, or other deformable material). The opening 931 can enlarge when the lead shaft is pressed through the opening, causing the opening 931 to grip and tighten about the lead shaft.

In some aspects, the ring structure 930 can be chemically or otherwise treated to increase its ability to deform and grip the lead shaft. For example, in one or more embodiments, the ring structure 930 can be swelled with Heptane or other solvent to receive the lead shaft, then shrunk (e.g., at room temperature or with application of heat) with the lead shaft in place, to securely incorporate the ring structure 930 at a selected position along a length of the lead shaft.

Depending on the implementation, one or multiple ring structures (e.g., ring structure 930 or other ring structure design) may be incorporated with or on a lead device. The number of ring structures which are deployed on a lead shaft can vary based on, for example, (i) a depth within the body of an electrode of a lead device including the lead shaft, (ii) a density or other physical characteristic of the tissue surrounding the lead device, (iii) a rigidness or flexibility of the ring structure (e.g., based on material properties, thickness, and surface formations of the ring structure(s)), and/or (iv) a radial dimension of the ring structure(s).

FIG. 9C-FIG. 9G illustrate variations of ring structures, according to one or more embodiments. In particular, structural modifications may be made to ring structures to adjust rigidity or flexibility of the ring structures. In some examples, the thickness of the ring structures may vary to adjust the rigidness/flexibility of the ring structure to a desired level.

Figure 9C:
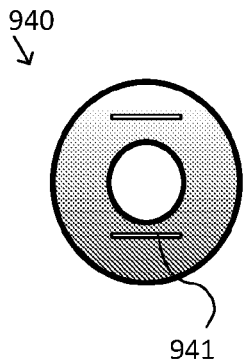

In an embodiment of FIG. 9C, a ring structure 940 may define one or more slits 941. The slits 941 reduce an overall ability of the ring structure 940 to resist migration in the short term by weakening a structural strength of the ring structure 940, and can increase an overall ability of the ring structure 940 to resist migration in the long term as tissue growth occurs through the slits 941. For example, without being bound by theory, initial placement may be more easily modified in the time before tissue growth occurs, to adjust position of a lead device incorporating the ring structure 940 for improved location of electrodes of the lead device; the tissue growth through the slits 941 may then more firmly anchor the lead device at the location later. A number, size, dimension, or location of each slit 941 can be used to impart various mechanical properties to the ring structure, for example, to modify the flexibility of the ring structure 940, so as to cause the ring structure 940 to be more or less capable of resisting migration by being less or more flexible, respectively.

Figure 9D:
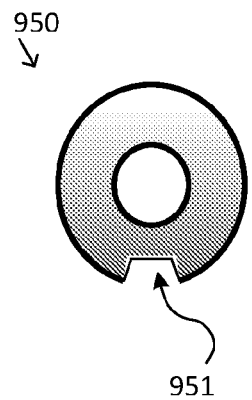

In an embodiment of FIG. 9D, a ring structure 950 may define one or more perimeter cut-outs 951. The perimeter cut-outs 951 reduce an overall ability of the ring structure 950 to resist migration. A number, size, dimension, shape, or location of each perimeter cut-out 951 can be used to impart various mechanical properties to the ring structure, for example, to modify the flexibility of the ring structure 950, so as to cause the ring structure 950 to be more or less capable of resisting migration by being less or more flexible, respectively.

Figure 9E:
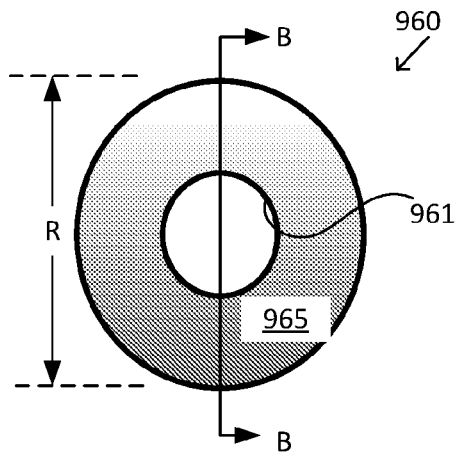
FIG. 9E, FIG. 9F, and FIG. 9G illustrate an example of an embodiment of a ring structure.
Figure 9F:
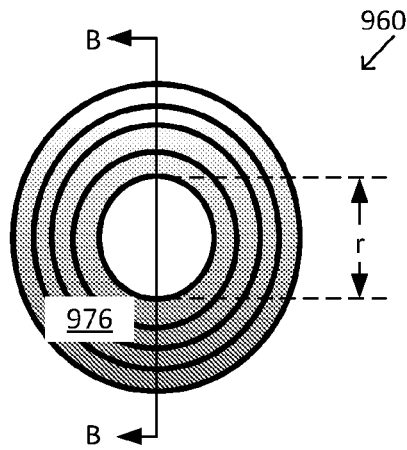
Figure 9G:
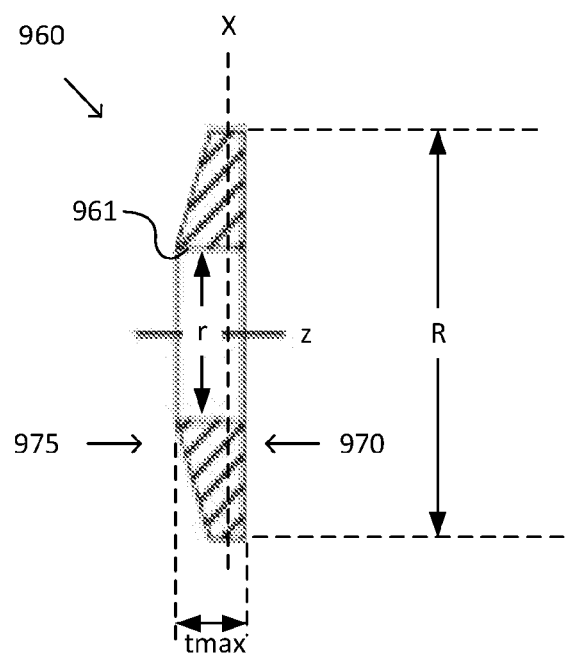

FIG. 9E-FIG. 9G illustrate a ring structure 960 for use with a lead device, according to one or more embodiments. FIG. 9E is a frontal view of the ring structure 960, FIG. 9F is a rear view of the ring structure 960, and FIG. 9G is an enlarged cross-sectional view of an embodiment of the ring structure 960 cut along line B-B in FIG. 9E and FIG. 9F. The ring structure 960 includes a front face 965 (FIG. 9E) at a front end 970 (FIG. 9G) and a back face 976 (FIG. 9F) at a back end 975 (FIG. 9G).

The ring structure 960 defines an opening 961 to receive a lead shaft. A radial dimension of the ring structure 960 can be a maximum (R) at the front face 965. The ring structure 960 may have a minimum radial dimension (r) at the back end 975. The ring structure 960 may be contoured, so that a radial dimension of the ring structure 960 increases along its axial length from the back end 975 to the front end 970, as indicated by the circular lines on FIG. 9F to illustrate an embodiment of contouring. In this and other embodiments, a radial dimension of the ring structure 960 can vary along an axis (Z) between the front end 970 and the back end 975.

A span between the front end 970 and the back end 975 may define a thickness (t) of the ring structure 960 to a maximum thickness (tmax). The ring structure 960 can be shaped so that the thickness of the ring structure 960 varies along a radial dimension of the ring structure 960, with the ring structure 960 having a maximum thickness at a region surrounding the opening 961 where the radial dimension is at a minimum (r), and a minimum thickness at a region where the radial dimension is at a maximum (R). The ring structure 960 may be symmetric with respect to axis (Z) as illustrated in FIG. 9E, FIG. 9F, and FIG. 9G, or may be asymmetric. The ring structure 960 may be asymmetric with respect to an axis perpendicular to axis (Z) (e.g., axis (X)), or may be symmetric.

As described with other examples, the ring structure 960 can be formed from elastomeric material, such as a silicone elastomer, polyurethane, or other deformable material. The material of the ring structure 960 can be selected so that the ring structure 960 has a desired flexibility or rigidness. Additionally, a thickness of the ring structure 960 can be selected to affect the flexibility or stiffness of the ring structure 960.

The varying thickness and radial dimension of the ring structure 960 can provide a structural orientation of the ring structure 960, where the structural orientation corresponds to an axial direction in which the ring structure 960 is most resistive of movement.

As noted, a lead shaft may be positioned in a body using an introducer or other apparatus.

Figure 10A:
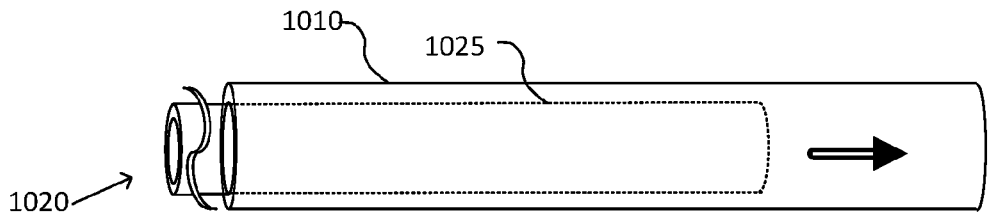
FIG. 10A illustrates an example of an embodiment of a lead device in an introducer.

FIG. 10A illustrates an example of an introducer 1010 positioned over a lead shaft 1025 of a lead device 1020. The lead device 1020 may include one or more anchoring mechanisms, such as, for example, any of the anchoring mechanisms illustrated and described herein (e.g., one or more notched anchor 220, 300, and/or 440, one or more wire structures 620, 630, 700, 770, 820, and/or 850, and/or one or more ring structures 920, 921, 922, 930, 940, 950, and/or 960).

Figure 10B:
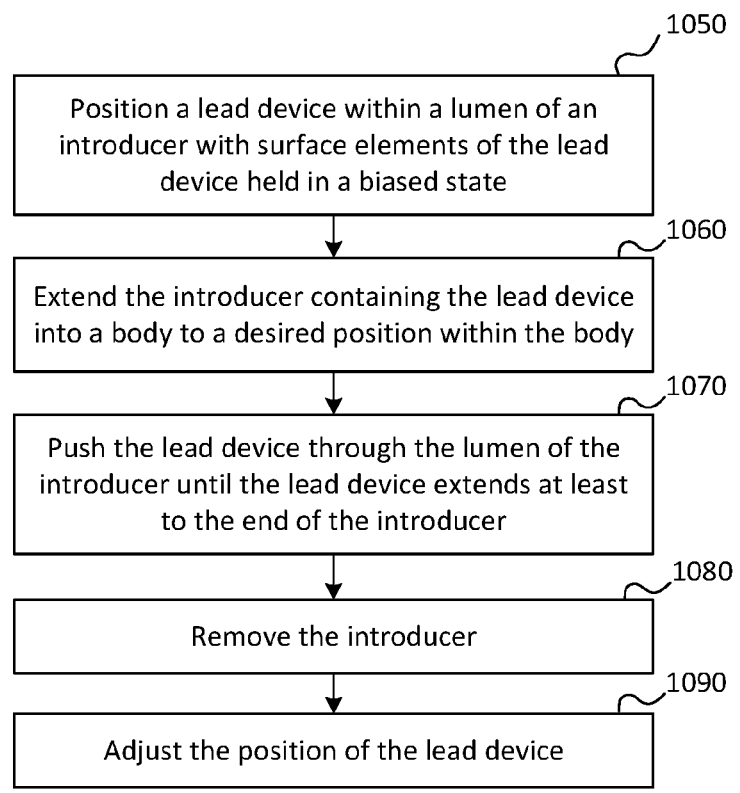
FIG. 10B illustrates an example of an embodiment of a method for introducing a lead device into a body.

FIG. 10B illustrates a method for implanting a lead device using an introducer such as the introducer 1010, according to one or more embodiments. At 1050, a lead device (e.g., an embodiment of the lead device 1020) is positioned within a lumen of an introducer (e.g., an embodiment of the introducer 1010) such that anchoring mechanisms on the lead device are biased by the introducer against their natural or relaxed state of protruding outwards from the lead device. An inner diameter of the introducer is sufficiently greater than an outer diameter of the lead device with the anchoring mechanisms biased against their natural or relaxed state to allow the lead shaft to be moved through the introducer when the introducer is at or near a desired position within the body. At 1060, the introducer is extended into the body and located within the body at the desired position. At 1070, the lead device is pushed through the lumen of the introducer until the lead device is at the end of the introducer or extends beyond the introducer. At 1080, the introducer is removed, leaving the lead device at approximately the desired position within the body. At 1090, the lead device is moved (e.g., axially) and tested until it is determined that the lead device is properly positioned. Alternatively, at 1070 the lead device is pushed through the lumen of the introducer until it extends out of the introducer sufficiently to adjust the position of the lead device at the desired position, such as by imaging a marker on a distal end of the lead device to aid in adjusting the position of the lead device (1090); then the introducer is removed (1080).

With reference to FIG. 10A, when the introducer 1010 is removed, the anchoring mechanisms of lead device 1020 can release outward to their respective unbiased state. When present in the tissue, the introducer 1010 can form a void within the tissue, such that the removal of the introducer 1010 allows the anchoring mechanisms to extend outward. The anchoring mechanisms can be formed from material that is sufficiently resilient to allow the anchoring mechanisms to return to or near their respective unbiased state when deployed. By way of example, such materials may include silicone elastomer, polyurethane (e.g., 65 D polyurethane, 75 D polyurethane or other polymeric compound) or NITINOL (or other elastic memory alloy). In one or more embodiments, the anchoring mechanisms are caused to enter the unbiased state by being subjected to pressure, force and/or heat.

According to one or more embodiments, at least a portion of a lead device may be formed from flexible or resilient material, such as silicone elastomer, polyurethane (e.g., 65 D polyurethane, 75 D polyurethane or other polymeric compound) or NITINOL (or other elastic memory alloy).

According to one or more embodiments, one or more of the anchoring mechanisms may include biodegradable materials. For example, an anchoring mechanism may be fully biodegradable to provide initial resistance to movement and subsequently little or no resistance to movement after degrading. For another example, an anchoring mechanism may be partially biodegradable to provide an initial structure, then a different structure later as the biodegradable portion degrades. Examples of biodegradable materials that may used in embodiments of the present disclosure include without limitation polymers (such as but not limited to poly(lactic acid) (PLA), poly(glycolic acid) (PGA), poly (lactic-co-glycolic acid) (PLGA), polyethylene glycol (PEG), polycaprolactone (PCL), a combination of any of the foregoing polymers with another material or materials, and combinations of any two or more of the foregoing), metals (such as but not limited to magnesium (Mg), iron (Fe), tungsten (W), zinc (Zn), yttrium (Y), neodymium (Nd), zirconium (Zr), palladium (Pd), manganese (Mn), a combination of any of the foregoing metals with another material or materials, an alloy of any the foregoing metals, or a combination of two or more of any of the foregoing), metallic glasses (such as but not limited to those based on strontium (Sr) or calcium (Ca)), starch, other biodegradable materials, and any combination of two or more of the foregoing. The biodegradable materials may be selected based on desired properties for a particular medical apparatus, such as rate of biodegradation, shear strength prior to or during biodegradation, brittleness, tensile strength, durability, bendability, manufacturability of the apparatus incorporating the biodegradable material(s), compatibility with other materials used in the apparatus, material stability (e.g., shelf life), temperature constraints, acidity constraints, and so forth.

According to one or more embodiments, whatever material is used to form an anchoring mechanism, one or more exterior surfaces of the anchoring mechanism may be roughened mechanically, thermally or chemically to increase the resistance of the anchoring mechanism to movement.

According to one or more embodiments, one or more exterior surfaces of an anchoring mechanism may be chemically coated to increase the resistance of the anchoring mechanism to movement and/or to promote tissue growth around the anchoring mechanism.

In any embodiment of the present disclosure, an optional coating may be applied over anchoring mechanisms, and/or an optional adhesive material may be applied between anchoring mechanisms and a lead shaft, to temporarily maintain a bias of the anchoring mechanism to facilitate placement within an introducer. Upon removal of an introducer from the body, the optional coating and/or optional adhesive material is exposed to body matter and dissolves. The dissolution rate can be designed to release the anchoring mechanisms from bias after a time, such as minutes, hours, or days after the introducer is removed. The optional coating and/or optional adhesive material can be, for example, any one or combination of the biodegradable materials discussed above.

In any embodiment of the present disclosure, geometry and size of the anchoring mechanisms may be adjusted to achieve the tissue engagement and holding power (resistance against movement) desired for the planned therapy.

Embodiments of the present disclosure include without limitation the following aspects:

In an aspect, a notched anchor for a lead device of a medical device includes a perimeter shell including a first end and a second end. The perimeter shell defines an interior space to receive a lead shaft. At least one of the first end or second end of the perimeter shell includes a notch formation that extends longitudinally from one of the first or second end, over a portion of a longitudinal length of the perimeter shell. In an embodiment, the first end of the perimeter shell includes a first pair of notch formations, each notch formation of the first pair extending towards the second end. In an embodiment, the second end of the perimeter shell includes a second pair of notch formations, each notch formation of the second pair extending towards the first end. Each notch of the first and second pairs may include a respective void that extends through a thickness of the perimeter shell. Each notch of the first and second pairs may be triangular. In an embodiment including the first pair and the second pair, the first pair of notches are offset from the second pair of notches by an offset angle. For example, the offset angle may range from 10 to 180 degrees. In an embodiment, the offset angle is about 90 degrees. In an embodiment, a thickness of the perimeter shell is substantially uniform across each of a radial length and a longitudinal length.

In an aspect, a lead device for a medical device includes a lead shaft and a perimeter shell including a first end and a second end, the perimeter shell defining an interior space to receive the lead shaft. At least one of the first end or second end of the perimeter shell includes a notch formation that extends longitudinally from one of the first or second end, over a portion of a longitudinal length of the perimeter shell. In an embodiment, the perimeter shell covers a portion of a fixation region of the lead shaft. In an embodiment, the perimeter shell is integrally formed with the lead shaft.

In an aspect, a method for forming a sleeve for a medical lead shaft includes: on a tubular length of sleeve material, forming, while the tubular length is in a first radial orientation, a first pair of voids, each void of the first pair being diametrically aligned; on the tubular length, forming, while the tubular length is in a second radial orientation, a second pair of voids, each void of the second pair being diametrically aligned; wherein the first pair of voids is longitudinally and radially offset from the second pair of voids; and segmenting the tubular length into a first segment that includes at least a portion of each void of the first pair and of the second pair.

In an aspect, a lead device for a medical apparatus includes a lead shaft and a wire structure affixed to the lead shaft, the wire structure including a flaring segment that extends outward in multiple directions from the lead shaft. In an embodiment, the wire structure includes a base structure that secures to the lead shaft. In an embodiment, the base structure includes one or more coils that are aligned to define an opening to receive the lead shaft. The lead shaft may be press-fitted into the opening defined by the coils. In an embodiment, the coils and the flaring segment form a continuous wire segment. In an embodiment, the flaring segment includes a stem and a distal tip, and a length of the flaring segment extending from the stem to the distal tip forms at least a partial loop. The partial loop may be in a range between a half-loop and a three-quarters loop. A cross-sectional dimension of the at least partial loop may range between 0.07 inches and 0.20 inches. In an embodiment, a diameter of a wire length used to form the flaring segment is between 0.008 inches to 0.010 inches. In an embodiment, the flaring segment is manipulatable between an expanded state and a contracted state. In the contracted state, a portion of the flaring segment may abut the lead shaft.

In an aspect, a wire structure to anchor a lead device in tissue includes a base structure to affix to a portion of the lead device, and a flaring segment that extends outward in multiple directions from the lead device. In an embodiment, the base structure includes multiple coils that are aligned to receive the portion of the lead device. In an embodiment, the flaring segment includes a stem and a distal tip, and wherein a length of the flaring segment extends from the stem to the distal tip to form at least a partial loop.

In an aspect, a method for operating a medical device includes: advancing an introduction device that retains a lead device through a patient's tissue, the lead device including a flaring segment that extends outward in multiple directions from the lead device, wherein the lead device is advanced until a tip portion of the lead device reaches a target region within the patient's tissue; when the lead device reaches the target region, removing the introduction device to expose the flaring segment; and optionally turning the flaring segment in the patient's tissue to anchor the lead device. In an embodiment, turning the flaring segment includes turning a portion of the lead device. In an embodiment, turning the flaring segment includes turning the portion of the lead device by a quarter-turn or half-turn. In an embodiment, the method further includes causing at least the flaring segment to expand into a partial loop structure within tissue in a body. In an embodiment, advancing the introduction device includes retaining, within the introduction device, the flaring segment in a contracted state, and wherein removing the introduction device causes the portion of the flaring segment to release into the expanded state.

In an aspect, a lead device for a treatment device includes a lead shaft and a set of one or more ring structures, each ring structure of the set being incorporated with or on the lead shaft. In an embodiment, the lead shaft includes a fixation region that is positioned a given length from a tip of the lead device, wherein each ring structure of the set is incorporated with or on the lead shaft in the fixation region. In an embodiment, a radial dimension of at least one ring structure of the set varies over a longitudinal length of the ring structure. In an embodiment, at least one ring structure of the set includes (i) a back end in which a radial dimension of the ring structure is at a minimum, and (ii) a front end in which a radial dimension of the ring structure is at a maximum. In an embodiment, at least one ring structure of the set includes a corresponding exterior ring face that has the maximum radial dimension. In an embodiment, the corresponding exterior ring face of at least one ring structure of the set is substantially flat. In an embodiment, at least one ring structure of the set tapers in radial dimension across at least a portion of a longitudinal length of the ring structure. In an embodiment, each ring structure of the set includes a corresponding exterior ring face that is predisposed to be bendable in a respective first axial direction and resist bending in a respective second axial direction. In an embodiment, the set of ring structures includes (i) a first ring structure having a first longitudinal orientation where the corresponding exterior ring face is predisposed to bend towards a tip of the lead device, and (ii) a second ring structure having a second longitudinal orientation where the corresponding exterior ring face is predisposed to bend away from the tip of the lead device. In an embodiment, each ring structure of the set is formed from a silicone elastomer or polyurethane. In an embodiment, the set of ring structures includes a first ring structure and a second ring structure, wherein the first ring structure and the second ring structure vary by at least one of a dimension or shape. In an embodiment, at least one ring structure of the set includes a corresponding exterior ring face having a maximum radial dimension in which a notch or cut-out is formed. In an embodiment, at least one ring structure of the set includes a corresponding exterior ring face having a maximum radial dimension in which a slit is formed.

In an aspect, a method for operating a medical apparatus includes: advancing an introduction device that retains a lead device through a body, the lead device including a lead shaft and a set of one or more ring structures; wherein the lead device is advanced until a tip of the lead device reaches a target region within the body; and when the lead device reaches the target region, removing the introduction device to cause each ring structure of the set of ring structures to release under bias, so that the ring structure expands to a maximum radial dimension of the ring structure. In an embodiment, the method further includes bending each of the one or more ring structures to fit within a lumen of the introduction device. In an embodiment, the method further includes forming a slit or opening at one or more locations of the ring structure.

In an aspect, a method for assembling a lead device includes: expanding a molded ring structure to increase a dimension of the ring structure's opening; receiving a lead body in the ring structure's opening while the ring structure is expanded; and causing the ring structure to contract from being expanded, to incorporate the ring structure on the lead body. In an embodiment, expanding the molded ring structure includes applying a chemical treatment to the ring structure to cause the ring structure to expand. In an embodiment, causing the ring structure to contract from the expanded includes allowing time for the ring structure to dry after applying the chemical treatment. In an embodiment, the method further includes forming a slit or cutout in the ring structure. In an embodiment, the method further includes molding the ring structure to be more bendable in a first axial direction, as compared to a second axial direction.

It is contemplated for examples described herein to extend to individual elements and concepts described herein, independently of other concepts, ideas or system, as well as for examples to include combinations of elements recited anywhere in this application. Although examples are described in detail herein with reference to the accompanying drawings, it is to be understood that the concepts are not limited to those precise examples. Accordingly, it is intended that the scope of the concepts be defined by the following claims and their equivalents. Furthermore, it is contemplated that a particular feature described either individually or as part of an example can be combined with other individually described features, or parts of other examples, even if the other features and examples make no mention of the particular feature. Thus, the absence of describing combinations should not preclude having rights to such combinations. Moreover, although described with respect to a lead device, the anchoring mechanisms of the present disclosure may be used for anchoring other medical implants, and although described with respect to medical implants, the anchoring mechanisms of the present disclosure may be used in other areas or fields.

What is claimed is:

1. A lead device of a medical device, the lead device comprising:
   a lead shaft; and
   a first anchoring mechanism disposed over the lead shaft such that the lead shaft is positioned within an opening defined by the first anchoring mechanism, the first anchoring mechanism including a notched anchor comprising a perimeter shell including a first end and a second end, the perimeter shell defining the opening to receive the lead shaft, wherein a first end of the perimeter shell comprises a first pair of notch formations, each notch formation of the first pair extending longitudinally from the first end toward the second end over a portion of a longitudinal length of the perimeter shell, and the second end of the perimeter shell comprises a second pair of notch formations, each notch formation of the second pair extending longitudinally from the second end toward the first end over a portion of the longitudinal length of the perimeter shell, wherein the first pair of notches are offset from the second pair of notches by an offset angle.

2. The lead device of claim 1, further comprising a second anchoring mechanism disposed over the lead shaft such that the lead shaft is positioned within the opening defined by the first anchoring mechanism and by an opening defined by the second anchoring mechanism.

3. The lead device of claim 2, wherein the second anchoring mechanism is a wire structure comprising a flaring segment that extends outward from the lead shaft.

4. The lead device of claim 3, wherein the wire structure comprises a base structure that secures to the lead shaft, and the base structure comprises one or more coils that are aligned to define the opening to receive the lead shaft.

5. The lead device of claim 4, wherein the one or more coils and the flaring segment form a continuous wire segment.

6. The lead device of claim 5, wherein the flaring segment includes a stem and a distal tip, and wherein a length of the flaring segment extending from the stem to the distal tip forms at least a partial loop.

7. The lead device of claim 6, wherein a length across the at least partial loop ranges between 0.07 inches and 0.20 inches.

8. The lead device of claim 3, wherein a diameter of a wire used to form the flaring segment is between 0.008 inches to 0.010 inches.

9. The lead device of claim 3, wherein the flaring segment is manipulatable between an expanded state and a contracted state, and, in the contracted state, a portion of the flaring segment abuts the lead shaft.

10. The lead device of claim 1, wherein the second anchoring mechanism is a ring structure.

11. The lead device of claim 10, wherein the lead shaft includes a fixation region that is positioned a given length from a tip of the lead device, wherein the ring structure is incorporated with or on the lead shaft in the fixation region.

12. The lead device of claim 10, wherein a radial dimension of the ring structure varies over a longitudinal length of the ring structure.

13. The lead device of claim 10, wherein the ring structure includes (i) a back end in which a radial dimension of the ring structure is at a minimum, and (ii) a front end in which a radial dimension of the ring structure is at a maximum.

14. The lead device of claim 13, wherein an exterior ring face of the front end of the ring structure is flat.

15. The lead device of claim 10, wherein the ring structure tapers in radial dimension across at least a portion of a longitudinal length of the ring structure.

16. The lead device of claim 10, wherein the ring structure includes a corresponding exterior ring face that is predisposed to be bendable in a first axial direction and resist bending in a second axial direction.

17. The notched anchor of claim 1, wherein the offset angle ranges from 10 to 180 degrees.

18. The notched anchor of claim 1, wherein the offset angle is 90 degrees.

* * * * *